(12) United States Patent
Koch et al.

(10) Patent No.: US 6,855,828 B1
(45) Date of Patent: Feb. 15, 2005

(54) DETECTION OF HYPOXIA

(75) Inventors: Cameron J. Koch, Aldan, PA (US); Alexander V. Kachur, Upper Darby, PA (US); Sydney M. Evans, Swarthmore, PA (US); Chyng-Yann Shiue, Villanova, PA (US); Ian R. Baird, Vancouver (CA); Kirsten A. Skov, Vancouver (CA); William R. Dolbier, Jr., Gainesville, FL (US); An-Rong Li, Gainesville, FL (US); Brian R. James, Vancouver (CA)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 165 days.

(21) Appl. No.: 09/648,306

(22) Filed: Aug. 25, 2000

Related U.S. Application Data

(60) Division of application No. 09/123,300, filed on Jul. 28, 1998, which is a continuation-in-part of application No. 08/598,752, filed on Feb. 8, 1996, now Pat. No. 5,843,404, which is a division of application No. 08/286,065, filed on Aug. 4, 1994, now Pat. No. 5,540,908, which is a continuation-in-part of application No. 07/978,918, filed on Nov. 19, 1992, now abandoned.

(51) Int. Cl.$^7$ ............................................. C07D 233/91
(52) U.S. Cl. ..................... 548/327.5; 435/1.1; 435/12.1; 436/57; 436/98; 436/124; 436/905
(58) Field of Search ..................... 514/398; 548/327.5; 435/1.1, 121; 436/57, 98, 124, 905

(56) References Cited

U.S. PATENT DOCUMENTS

| | | | |
|---|---|---|---|
| 3,505,349 A | 4/1970 | Beaman et al. | 260/309 |
| 3,679,698 A | 7/1972 | Beaman et al. | 548/327.5 |
| 4,241,060 A | 12/1980 | Smithen | 374/212 |
| 4,371,540 A | 2/1983 | Lee et al. | 424/273 R |
| 4,797,397 A | 1/1989 | Suto et al. | 514/212 |
| 4,816,401 A | 3/1989 | Taupier et al. | 435/240.31 |
| 4,927,941 A | 5/1990 | Kagiya et al. | 548/264.8 |
| 4,977,273 A | 12/1990 | Kagiya et al. | 548/339 |
| 5,030,036 A | 7/1991 | Huff et al. | 405/266 |
| 5,086,068 A * | 2/1992 | Raleigh et al. | 514/398 |
| 5,304,654 A * | 4/1994 | Kagiya et al. | 548/327.5 |
| 5,540,908 A * | 7/1996 | Koch et al. | 424/9.34 |
| 5,721,265 A | 2/1998 | Tracy et al. | 514/396 |
| 5,843,404 A | 12/1998 | Koch et al. | 424/934 |

FOREIGN PATENT DOCUMENTS

WO   WO 01/12575 A1   2/2001

OTHER PUBLICATIONS

Adams, "Hypoxia–Mediated Drugs for Radiation and Chemotherapy", *Cancer*, 1981, 48, 696–707.
Beaman et al., "Studies in the nitromidazole series. III. 2–Nitro–imidiazole dderivatives substituted in the 1–position", Chemical Abstract 71(5): 22065t, 1967, p. 22060.

Chapman et al., "The Fraction of Hypoxic Clonogenic Cells in Tumor Populations", *Biol. Bases Clin. Imp. Tum. Rad.*, G.H. Fletcher, C. Nevil, & H.R. Withers, (eds.), 1983, 61–73.
Chapman et al., "Keynote Address: Cellular Reduction of Nitroimidazole Drugs: Potential for Selective Chemotherapy and Diagnosis of Hypoxic Cells", *Int. J. Radiation Oncol. Biol. Phys.*, 1989, 16, 911–917.
Franko et al., "Oxygen Supply to Spheroids in Spinner and Liquid–Overlay Culture", Recent Results in *Cancer Res.* in 94" Culture of Cellular Spheroids 62, 1984, 95, 162–167.
Grunberg et al., "Antiprotozoan and antibacterial activity of 2–nitro–imidazole derivatives", Chemical Abstract 70(3):10175v, 1968, p. 10174.
Heindel et al, "Macromolecular Attachment as a Metabolic Stabilizer for a Labile Radiosensitizer", *J. Pharm. Sci.*, 1987, 76(5), 384–386.
Kohler et al., "Continuous cultures of fused cells secreting antibody of predefined specificity", *Nature*, 1975, 256, 495–497.
Knauf et al., "Monoclonal antibodies against human ovarian tumor asociated antigen NB/70K: Preparation and use in a radioimmunoassay for measuring NB/70K in serum", *Cancer Immunol. Immunother.*, 1986, 21, 217–225.
Raleigh et al., "Reductive Fragmentation of 2–Nitroimidazoles: Amines and Aldehydes", *Int. J. Radiation Oncol. Biol. Phys.*, 1984, 10, 1337–1340.
Raleigh et al., "Fluorescence immunohistochemical detection of hypoxic cells in spheroids and tumours," *Br. J. Cancer*, 1987, 56, 395–400.
Taylor et al., "Differences in the toxicity and Metabolism of the 2–Nitroimidazole Misonidazole (Ro–07–0582) in HeLa and Chinese Hamster Ovary Cells", *Cancer Res.*, 1978, 38, 2745–2752.
Urtasun et al., "A novel technique for measuring human tissue pO$_2$ at the cellular level", *Br. J. Cancer*, 1986, 54, 453–457.
Varghese et al., "Binding to Cellular Macromolecules as a Possible Mechanism for the Cytotoxicity of Misonidazole", *Cancer Res.*, 1980, 40, 2165–2169.
Lord, et al., "Detection of Hypoxic Cells by Monoclonal Antibody Recognizing 2–Nitroimidazole Adducts", *Cancer Res.*, 1993, 53, 5721–5726.

(List continued on next page.)

*Primary Examiner*—Ceila Chang
*Assistant Examiner*—Sonya Wright
(74) *Attorney, Agent, or Firm*—Woodcock Washburn LLP

(57) ABSTRACT

Nitroaromatic compounds and immunogenic conjugates comprising a novel nitroaromatic compound and a carrier protein are disclosed. The invention further presents monoclonal antibodies highly specific for the claimed nitroaromatic compounds, the compounds' protein conjugates, the compounds' reductive byproducts, and adducts formed between the compounds and mammalian hypoxic cell tissue proteins. The invention is further directed to methods for detecting tissue hypoxia using immunohistological techniques, non-invasive nuclear medicinal methods, or nuclear magnetic resonance. Diagnostic kits useful in practicing the methods of claimed invention are also provided.

9 Claims, 5 Drawing Sheets

OTHER PUBLICATIONS

Franko, A.J. et al., "Oxygen dependence of binding of misonidazole to rodent and human tumors in vitro", *Cancer Res.*, 1987, 47, 5367–5376.

Harwell et al., *J. Immunol. Methods*, 1984, 66, 59–67.

Kennedy et al., *Biochem. Pharm.*, 1980, 29, 1–8.

Koch, C.J., "A thin–film culturing technique allowing rapid gas–liquid equilibration (6 seconds) with no toxicity to mammalian cells", *Radiat. Res.*, 1984, 97, 434–442.

Koch, C.J. et al., "Metabolism induced binding of 14C–misonidazole to hypoxic cells: kinetic dependence on oxygen concentration an dmisonidazole concentration", *Int. J. Radiation Oncology Biol. Phys.*, 1984, 10, 1327–1332.

Koch, C.J. et al., "Radiolytic Reduction of Protein and Nonprotien Disulfides in the Presence of Formate: A Chain Reaction", *Arch. Biochem. Biophys.*, 1991, 287, 75–84.

Moulder, J.E. et al., "Hypoxic fractions of solid tumors: experimental techniques, methods of analysis and a survey of existing data", *Int. J. Radioat. Oncol. Biol. Phys.* 1984, 10, 695–712.

Parliament et al., "Non–invasive assessment of human tumour hypoxia with [123]I–iodoazomycin arabinoside: preliminary report of a clinical study", *Br. J. Cancer*, 1992, 65, 90–95.

Rasey et al., "Characterization of Radiolabeled Fluoromisonidazole as a Probe for Hypoxic Cells", *Radiation Res.*, 1987, 111, 292–304.

Koch, C.J., "The reductive activation of nitroimidazoles; modification by oxygen and other redox–active molecules in cellular systems", *Selective Activation of Drugs by Redox Processes*, 1990, *NATO Series A 198*, 237–247.

Arteel, GE et al., "Evidence that hypoxia markers detect oxygen gradients in liver: pimonidazole and retrograde perfusion of rat liver", *British J. Cancer*, 1995, 72(4), 889–895.

Raleigh et al., "Importance Of Thiols In The Reductive Binding of 2–Nitroimidazoles to Macromolecules", *Biochem. Pharmacol.*, 1990, 40, 2457–2464.

Tewson, T.J., "Synthesis of [18F] Fluoroetanidazole: a potential new tracer for imaging hypoxia", *Nucl. Med. Biol.*, 1997, 24(8), 755–760.

Hamacher et al., "Efficient Stereospecific Synthesis of No–Carrier–Added 2–[18F]–Fluoro–2–Deoxy–D–Glucose Using Aminopolyether Supported Nucleophilic Substitution", *J. Nucl. Med.*, 1986, 27(2), 235–238.

Adams, G.E., "Selective Activation of Drugs by Redox Processes", *NATO Series A 198*, 1990.

Bialik, S. et al., "Myocyte apoptosis during acute myocardial infarction in the mouse localizes to hypoxic regions but occurs independently of p53", *J. Clin. Investig.*, 1997, 100, 1363–1372.

Brizel, D.M. et al., "Tissue oxygenation predicts for the likelihood of distant metastases in human soft tissue sarcoma", *Cancer Res.*, 1996, 56, 941–943.

Brizel, D.M. et al., "Pretreatment oxygenation profiles of human soft tissue sarcomas", *Int. J. Radiat. Oncol. Biol. Phys.*, 1994, 30, 635–642.

Brizel, D.M. et al., "Tumor hypoxia adversely affects the prognosis of carcinoma of the head and neck", *Int. J. Radiat. Oncol. Biol. Phys.*,1997, 38, 285–289.

Brown, J.M. et al., "SR–2508: a 2–nitroimidazole amide which should be superior to misonidazole as a radiosensitizer for clinical use", *Int. J. Radiat. Oncol. Biol. Phys.*, 1981, 7, 695–703.

Cater, D.B. et al., "Quantitative meaurements of oxygen tensions in normal tissues and in the tumors of patients before and after radiotherapy", *Acta. Radiol.*, 1960, 23, 233–256.

Chapman, J.D. et al., "Characteristics of the metabolism–induced binding of misonidazole to hypoxic mammalian cells", *Cancer Res.*, 1983, 45, 1523–1528.

Clyman, R.I. et al., "Permanent anaotomic closure of the newborn ductus arteriosus: the roles of postnatal constriction, hypoxia and gestation", New Eng. J. Med., Submitted, 1997.

Cobb, L.M. et al., "Microscopic distribution of misonidazole in mouse tissues", *Br. J. Cancer*, 1989, 59, 12–16.

Cobb, L.M. et al., "Retention of misonidazole in normal and malignant tissues: interplay of hypoxia and reductases", *Int. J. Rad. Onc. Biol. Phys.*, 19982, 22, 655–659.

Coleman, C.N. et al., "Relationship between the neurotoxicity of the hypoxic cell radiosensitizer SR 2508 and the pharmacokinetic profile", *Cancer Res.*, 1987, 47, 319–322.

Coleman, C.N. et al., "Initial pharmacology and toxicology of intravenous desmethylmisonidazole", *Int. J. Radiat. Oncol. Biol. Phys.*, 1982, 8, 371–375.

Evans, S.M. et al., "Use of power Doppler ultrasound guided biopsies to locate regions of tumour hypoxia", Brit. J. Cancer, In Press, 1997.

Evans, S.M. et al., "Evaluation of the concept of "hypoxic fraction" as a descriptor of tumor oxygenation status", Adv. Exptl. Biol. Med., In Press, 1995.

Evans, S.M. et al., "Tamoxifen induces hypoxia in MCF–7 xenografts", Cancer Res., In Press, 1997.

Evans, S.M. et al., "Radiation response and other characteristics of the 9L rat glioma grown as an epigastric tissue isolate", Radiat. Oncol. Invest., 1994, 2, 134–143.

Evans, S.M. et al., "Imaging hypoxia in diseased tissues", Adv. Exptl. Biol. Med., In Press, 1996.

Evans, S.M. et al., "Identification of hypoxia in cells and tissues of epigastric 9L rat glioma using EF5 [2–(2–nitro–1H–imidazol–1–yl)–N–(2,2,3,3,3–pentafluoropropyl)acetamide]", Br. J. Cancer, 1995, 72, 875–882.

Evans, S.M. et al., "2–nitroimidazole (EF5) binding predicts radiation sensitivity in individual 9L subcutaneous tumors", *Cancer Res.*, 1996, 56, 405–411.

Franko, A.J. et al., "Binding of misonidazole to V79 spheroids and fragments of Dunning rat prostate and human colon carcinoma in vitro: diffusion of oxygen and reactive metabolites", *Int. J. Radiat. Oncol. Biol. Phys.*, 1984, 10, 1333–1337.

Garrecht, B.M. et al., "The labelling of EMT–6 tumors in Balb/c mice with 14C–misonidazole", *Brit. J. Radiol.*, 1983, 56, 745–753.

Gatenby, R.A. et al., "Oxygen tension in human tumors: in vivo mapping using CT–guided probes", *Radiol.*, 1985, 156, 211–214.

Gatenby, R.A. et al., "Oxygen distribution in squamous cell carcinoma metastases and its relationship to outcome of therapy", *Int. J. Radiat. Oncol. Biol. Phys.*, 1988, 14, 831–838.

Graeber, T.G. et al., "Hypoxia–mediated selection of cells with diminished apoptotic potential in solid tumours", Nature, 1996, 379, 88–91.

Hirst, D.G. et al., "Changes in misonidazole binding with hypoxic fraction in mouse tumors", *Int. J. Radiat. Biol. Oncol. Phys.*, 1984, 11, 1349–1355.

Hockel, M. et al., "Association between tumor hypoxia and malignant progression in advanced cancer of the uterine cervix", Cancer Res., 1996, 56, 4509–4515.

Hockel, M. et al., "Intratumor pO2 predicts survival in advanced cancer of the uterine cervix", Radiotherapy and Oncology, 1993, 26, 45–50.

Hodgkiss, R.J. et al., "Flow cytometric evaluation of hypoxic cells in solid experimental tumours using fluorescence immunodetection", Br. J. Cancer, 1991, 63, 119–125.

Horsman, M.R. et al., "Relationship between radiobiological hypoxia and direct estimates of tumour oxygenation in a mouse tumour model", Radiother. Oncol., 1993, 28, 69–71.

Kennedy, K.A. et al., "Preferential activation of mitomycin C to cytotoxic metabolites by hypoxic tumor cells", Cancer Res., 1980, 40, 2356–2360.

Koch, C.J. et al., "Cysteine concentrations in rodent tumors: unexpectedly high values may cause therapy resistance", Int. J. Cancer, 1996, 67, 661–667.

Koch, C.J. et al., "Oxygen dependence of cellular uptake of EF5 [2–(2–nitro–1H–imidazol–1–yl)–N–(2,2,3,3,3–pentafluoropropyl)acetamide]: analysis of drug adducts by fluorescent antibodies vs bound radioactivity", Br. J. Cancer, 1995, 72, 869–874.

Koch, C.J. et al., Imaging hypoxia and blood flow in normal tissues, Adv. Exptl. Biol. Med., In Press, 1996.

Koch, C.J. et al., "Detection of hypoxic cells by monoclonal antibody recognizing 2–nitroimidazole adducts." United States Patent, Continuation In Part, Submitted 1996.

Koch, C.J. et al.,"Comment on the Hypothesis that Hyperthermia Facilitates Reoxygenation." Int. J. Hyperthermia, 1995, 11, 447–450.

Laughlin, K.M. et al., "Biodistribution of the nitroimidazole EF5 [2–(2–nitro–iH–imidazole–ly)–N–(2,2,3,3,3,–pentafluoropropyl)–acetamide]in mice bearing subcutaneous EMT6 tumors",J. Pharmacol. Exptl. Therapeut., 1996, 277, 1049–1057.

Lee, J. et al., "Direct relationship between radiobiological hypoxia in tumors and monoclonal antibody detection of EF5 cellular adducts", Int. J. Cancer, 1996, 67, 372–378.

Matthews, J. et al., "Immunocytochemical labelling of aerobic and hypoxic mammalian cells using a platinated derivative of EF5", Brit. J. Cancer, 1996, 73, S200–S203.

Nordsmark, M. et al., "Pretreatment oxygenation predicts radiation response in advanced squamous cell carcinoma of the head and neck", Radioth. and Oncol., 1996, 41, 31–39.

Nozue, M. et al., "Interlaboratory variation in oxygen tension measurement by Eppendorf "Histograph" and comparison with hypoxic marker", J. Surg. Oncol.,1997, 66, 30–38.

Okunieff, P. et al., "Oxygen tension distributions are sufficient to explain the local response of human brest tumors treated with radiation alone", Int. J. Radiat. Biol. Oncol. Phys. 1993, 26, 631–636.

Olive, P.L. et al., "Hypoxic fractions measured in murine tumors and normal tissues using the comet assay", Int. J. Radiat. Oncol. Biol. Phys., 1994, 29, 487–491.

Rampling, R. et al., "Direct measurement of pO2 distribution and bioreductive enzymes in human malignant brain tumors", Int. J. Rad. Onc. Biol. Phys., 1994, 29, 427–431.

Rasey, J.S. et al., "Characteristics of the binding of labeled fluoromisonidazole in cells in vitro", Radiat. Res., 1990, 122, 301–308.

Schwentker, A. et al., "A model of wound healing in chronically radiation–damaged rat skin: the effect of hyperbaric oxygen", Int. J. Radiat. Oncol. Biol. Phys., Submitted, 1997.

Shapiro, I.M. et al., "Chondrocytes in the endochondral growth cartilage are not hypoxic", Am. J. Physiol., 1997, 272, cll34–cll43.

Shibamoto, Y. et al., "A phase I study of a hypoxic cell sensitizer KU–2285 in combination with conventional radiotherapy", Radither. & Oncol. 1996, 40, 55–58.

Siim, B.G. et al., "Tirapazamine–induced cytotoxicity and DNA damage in trasplanted tumors: relationship to tumor hypoxia", Cancer Res., 1997, 57, 2922–2928.

Stone, H.B. et al., "Oxygen in human tumors: Correlation between Methods of Measurement and Response to Therapy", Radiat. Res., 1993, 136, 422–434.

Thomlinson, R.H. et al., "The histological structure of some human lung cancers and the possible implications for radiotherapy", Br. J. Cancer, 1955, 9, 539–579.

Van Os–Corby, D.J. et al., "Is misonidazole binding to mouse tissues a measure of cellular pO2?", Biochem. Pharmacol., 1987a, 36, 3487–3494.

Varghese, A.J. et al., "Hypoxia–dependent reduction of 1–(2–nitro–1–imidazolyl)–3–methoxy–2–propanol by Chinese hamster ovary cells and KHT tumor cells in vitro and in vivo", Cancer Res., 1976, 36, 3761–3765.

Waleh, N.S. et al., "Mapping of the vascular endothelial growth factor–producing hypoxic cells in multicellular tumor spheroids using a hypoxia–specific marker", Cancer Res., 1995, 55, 6222–6226.

Wendling, P. et al., "Heterogeneous oxygenation of rectal carcinomas in humans. A critical parameter for pre–operative irradiation",Adv. Exp. Med. Biol., 1984, 180, 293–300.

Woods, M.R. et al., "Detection of individual hypoxic cells in multicellular spheroids by flow cytometery using the 2–nitroimidazole EF5, and monoclonal antibodies", Int. J. Radiat. Oncol. Biol. Phys., 1996, 34, 93–101.

Wouters, B.G. et al., "Cells at intermediate oxygen levels can be more important than the "hypoxic fraction" in determining tumor response to fractionated radiation therapy", Radiat. Res., 1997, 147, 541–550.

Zeman, E.M. et al., "The relationship between proliferative and oxygenation status in spontaneous canine tumors", Int. J. Rad. Oncol. Biol. Phys., 1993, 27, 891–898.

* cited by examiner

Figure 2. HPLC analysis of [$^{18}$F]EF-1 with simultaneous detection of 325 nm absorbency (upper curve) and radioactivity (lower curve).

Figure 3. Effect of $[KKr]F_{0.7}(CO_3)_{0.15}$ to $EBr1$ ratio on the EF1 yield.

DETECTION OF HYPOXIA

RELATED APPLICATIONS

This Application is a divisional of U.S. application Ser. No. 09/123,300 filed Jul. 28, 1998 which is a continuation in part of application Ser. No. 08/598,752, filed on Feb. 8, 1996, now U.S. Pat. No. 5,843,404, which is a divisional of Ser. No. 08/286,065 filed Aug. 4, 1994 now U.S. Pat. No. 5,540,908, which is a continuation in part of Ser. No. 07/978,918 filed Nov. 19, 1992 now abandoned.

FIELD OF THE INVENTION

This invention generally relates to a class of nitroaromatic compounds that, when activated by reductive metabolism, bind to hypoxic cells. This reductive metabolism and binding increase as the oxygen concentration of cells decreases, which enables these compounds to be used as indicators of hypoxia. The present invention presents novel nitroaromatic compounds; immunogenic conjugates comprising the novel nitroaromatic compounds and proteins; and monoclonal antibodies specific for the novel nitroaromatic compounds of the invention, their protein conjugates, their reductive byproducts, and adducts formed between mammalian hypoxic cells and the compounds of the invention. The invention is further directed to methods for detecting levels of low oxygen in tissue. Detection may be done directly using methods such as imaging techniques involving specific isotopes attached to the nitroaromatic drug, or indirectly using the monoclonal antibodies (mAbs) in immunohistological assays. Still further, the present invention is directed to kits for performing the methods of the invention.

BACKGROUND OF THE INVENTION

One of the most important goals in oncology is the identification and elimination of treatment resistant cells; hypoxic cells are the most familiar examples of this type of cell. Kennedy, et al., *Biochem. Pharm.* 1980, 29, 1; Moulder, et al., *Int. J. Radioat. Oncol. Biol. Phys.* 1984, 10, 695; Adams, *Cancer*, 1981, 48, 696. Hypoxic cells are seldom found in normal tissues, and are generally found only in conjunction with certain tumors, vascular diseases, or after a stroke.

As certain tumors enlarge, the tissue often outgrows its oxygen and nutrient supply because of an inadequate network of functioning blood vessels and capillaries. Although the cells deprived of oxygen and nutrients may ultimately die, at any given time a tumor may produce viable hypoxic cells. These hypoxic cells, although alive, have very low oxygen concentrations because of their remoteness from the blood vessels.

The level of molecular oxygen has important implications in disease diagnosis, and prognosis. In medical oncology, for example, hypoxic cells in solid tumors may be highly resistant to killing by some forms of chemotherapy. When chemotherapeutic agents are administered to patients, the agents are carried through the functioning blood vessels and capillaries to the target tissue. Because hypoxic tissue lacks a fully functioning blood supply network, the chemotherapeutic drugs may never reach the hypoxic cells; instead, intervening cells scavenge the drug. The result is that the hypoxic cells survive and recurrence of the tumor is possible. Kennedy, et al., supra.

Tissue hypoxia also hinders the effectiveness of radiation therapy, especially of neoplasms. Radiation treatment is most effective in destroying oxygen containing cells because oxygen is an excellent radiation sensitizer. The presence of hypoxic cells impedes this treatment because their low oxygen concentration renders the ionizing radiation relatively ineffective in killing the cancerous cells. Therefore, hypoxic cells are more likely to survive radiation therapy and eventually lead to the reappearance of the tumor. The importance of hypoxic cells in limiting radiation responsiveness in animal tumors is well known, Adams, supra; Moulder, et al., supra; Chapman, et al., "*The Fraction of Hypoxic Clonogenic Cells in Tumor Populations,*" in *Biological Bases and Clinical Implications of Tumor Radioresistance* 61, G. R Fletcher, C. Nevil, & H. R Withers, eds., 1983. Studies have revealed that such resistant cells greatly affect the ability of radiation and chemotherapy to successfully sterilize tumors in animals. Substantial work since that time has shown similar problems in human tumors. Despite the progress in animal studies regarding the identification of hypoxic cells, limited success has been achieved in humans. One reason for this disparity may relate to differences in tumor growth and other host related factors, but in addition, there has been no suitably accurate method to assess tissue oxygen at a sufficiently fine resolution Venous oxygen pressure is generally ~35 Torr, an oxygen level providing nearly full radiation sensitivity. As the oxygen level decreases below 35 Torr, radiation resistance gradually increases, with half-maximal resistance at about 3.5 Torr, and full resistance at about 0.35 Torr. Therefore, it is necessary to measure much lower oxygen levels than are usually encountered in normal tissue. Current technology does not meet this need. Oxygen partial pressure measured using current techniques often yields an average value for large numbers of neighboring cells. This is a severe impediment for detection and diagnosis because histological evaluation of solid tumors suggest that important changes in cellular oxygen can occur over dimensions of even a few cell diameters. Urtasun, et al., *Br. J. Cancer*, 1986, 54, 453. Nitroheterocyclic drugs have been under extensive investigation as oxygen indicators. It is known that this class of compounds has the potential for resolution at the cellular level and can provide sufficient sensitivity to monitor the low oxygen partial pressures described above. This technique involves the administration of nitroaromatic drugs to the tissue of interest. The drugs undergo bioreductive metabolism at a rate which increases substantially as the tissue's oxygen partial pressure decreases. The result of this bioreductive metabolism is that reactive drug products are formed which combine chemically to form adducts with predominantly cellular proteins. Because the metabolic binding of these compounds to cellular macromolecules is inhibited by oxygen, these compounds bind to hypoxic cells in preference to normal healthy, oxygen-rich tissue. This preferential metabolic binding, or adduct formation, provides a measure of the degree of hypoxia Koch, et al., Int. *J. Radiation Oncology Biol. Phys.*, 1984, 10, 1327.

Misonidazole (MISO) 3-methoxy-1-(2-nitroimidazol-1-yl)-2-propanol, and certain of its derivatives have been under extensive investigation as indicators of hypoxia in mammalian tissue. Chapman, et al., *Int. J. Radial. Oncol. Biol. Phys.*, 1989,16, 911; Taylor, et al., *Cancer Res.*, 1978, 38,2745; Varghese, et al., *Cancer Res.*, 1980, 40,2165. The ability of certain minidazole derivatives to form adducts with cellular macromolecules, referred to as binding throughout this application, has formed the basis of various detection methods.

For example, $^3H$ or $^{14}C$ labeled misonidazole has been used in vitro and in vivo, with binding analyzed by liquid scintillation counting or autoradiography. Chapman, 1984 supra; Urtasun, 1986, supra; Franko, et al., *Cancer Res.*, 1987, 47, 5367. A monofluorinated derivative of misonidazole has utilized the positron emitting isotope F18 for imaging bound drug in vivo, Rasey, et al., *Radiat. Res.*, 1987, 111,292. The method of the preparation of the PET derivative of ethanidazole was described in Tewson T. J. Synthesis of [$^{18}$F] Fluoroetanidazole: a potential new tracer for imaging hypoxia *Nuclear Medicine & Biology*, 24(8): 755–60, 1997.

A hexafluorinated derivative of misonidazole (1-(2-hydroxy-3-hexafluoro-isopropoxy-propyl)-2-nitroimidazole has been assayed directly (no radioactive isotopes) via nuclear magnetic resonance spectroscopy (NMR or MR) techniques. Raleigh, et al., *Int. J. Radiat. Oncol Biol. Phys.*, 1984, 10, 1337. Polyclonal antibodies to this same derivative have allowed immunohistochemical identification of drug adducts. Raleigh, et al., *Br. J. Cancer*, 1987, 56, 395. An iodine isotope has been incorporated into another azomycin derivative, azomycin arabinoside, allowing radiology techniques of detection. Parliament, et al., *Br. J. Cancer*, 1992, 65, 90.

A fluorescence immunohistochemical assay for detecting hypoxia is described in the literature. Raleigh, et al., 1987, supra. A method for preparing immunogenic conjugates for use in such assays is broadly disclosed in U.S. Pat. No. 5,086,068, issued to Raleigh, et al., on Feb. 4, 1992 ("Raleigh patent"). The Raleigh patent describes a method for preparing an immunogenic conjugate comprising a known fluorinated misonidazole derivative and an immunogenic carrier protein, hemocyanin. The compound used in this method (CCI-103F) was a hexafluorinated derivative of 2-nitroimidazole misonidazole, described above in connection with NMR studies.

The resulting conjugate is used to raise rabbit polyclonal antibodies specific for the misonidazole derivative. Fluorescence immunohistochemical studies showed that the polyclonal antibodies bound to hypoxic (central) regions of spheroids (a multicellular aggregate of cells in tissue culture having some properties more closely related to tumors) and tumor sections in patterns similar to those revealed by audioradiographic studies using radioactive drug alone, i.e. without polyclonal antibodies.

However, polyclonal antibodies are plagued by numerous difficulties such as cross-reactivity, lack of specificity, insensitivity, inability to purify the actual antibodies of interest, and highly unstable supply.

The Raleigh patent's technology, of conjugating a small antigen to a large carrier protein to elicit an immune response, is a central basis of antibody production and is well known in the art. Those skilled in the art would also appreciate that nitroaromatic must be activated by chemical or biochemical reduction to cause adducts to form with cellular macromolecules. Further, it has not been possible to produce monoclonal antibodies using the methods described in the Raleigh patent and paper (Raleigh et al., 1987, supra).

The Raleigh patent discloses immunogenic conjugates useful for producing polyclonal antibodies, but data generated using the patent's teachings has produced variable results, problematic in a detection technique. Furthermore, independent experimentation performed according to the Raleigh patent's methods did not reproduce the high degree of conjugation between the misonidazole derivatives and the protein as was claimed. See, e.g., U.S. Pat. No. 5,540,908, the disclosures of which are herein incorporated by reference in their entirety.

The bioreductive drug assays described above do not directly measure oxygen partial pressure, even though this is the required value, using the example of radiation therapy to predict radiation response. Rather, the assays measure adduct formation, a biochemical process which is inhibited by oxygen. The data generated using these methods has shown that the degree of inhibition by oxygen varies substantially from tissue to tissue. Franko, et al., 1987, supra. Furthermore, the maximum rate of adduct formation in the complete absence of oxygen is also highly variable from tissue to tissue, as is the maximum percentage of inhibition by oxygen, Koch, *in Selective Activation of Drugs by Redox Processes*, Plenum Press, pp. 237–247, Adams, et al., eds, New York, 1990. Another way of expressing these limitations is that the bioreductive formation of nitroaromatics provide only a relative indication of varying oxygen levels, but is inadequate at providing an absolute measurement of oxygen partial pressure because there are several factors which affect adduct formation in addition to changes in oxygen, non-oxygen-dependent factors. Additionally, the choice of nitroaromatic drug affects the variability related to the non-oxygen-dependent factors.

Early research efforts (i.e., before the invention claimed in U.S. Pat. No. 5,540,908 on Nov. 19, 1992) had focused on misonidazole and certain of its derivatives. However, misonidazole is the most susceptible of several drugs tested to non-oxygen-dependent variations in adduct formation. Koch, Selective Activation, supra. Other problems relate to various physicocherrmical properties of existing drugs, all of which can influence the non-oxygen dependent variations in adduct formation. For example, the hexafluorinated misonidazole derivative described above had a high degree of insolubility.

Although 2-nitroimidazoles labeled with radiochemnical tracers such as tritium and $^{14}$C provide a sensitive method for detecting tissue hypoxia using autoradiographic methods, the biohazards and costs associated with these techniques are a significant drawback. The amount of radioactivity associated with the administration of such labeled drugs, which still requires a tissue biopsy, becomes a substantial problem in animal studies, and an even greater problem in humans where 30 millicuries of tritiated drug are typically used. Urtasun, et al., 1986, supra. $^{14}$C is prohibitively expensive and causes unacceptable radiation exposures. The use of such radioactive tracers is generally not acceptable because of the stringent requirements associated with handling radioactive tissues and bodily fluids. There are also practical limitations to the use of radioactive tracers. For example, the delay required for audioradiographic analysis of the tissue sections, often several weeks, is a very serious impediment to the rapid analysis required in treatment determination. Moreover, toxicity problems associated with certain misonidazole derivatives resulted in the drug being administered at a relatively low concentration, which decreased detection sensitivity. Thus, to utilize the high sensitivity of radioactive drug methods, short-lived isotopes analyzable by non-invasive methods such as PET and SPECT are preferred; there is still a need for such methods.

Many human and animal diseases are characterized by the pathological formation of tissue hypoxia and ischemia. Hypoxic cells in solid tumors have been associated with treatment resistance by radiation, Moulder, supra, and some forms of chemotherapy, Kennedy, supra. Treatment of such conditions can only be optimized by determining the extent and degree of hypoxia in the affected tissues of individual patients. Accordingly, there is a great oncological need to identify hypoxic cells.

While biopsy-based methods are applicable to many forms of analysis in tumors, non-invasive assays are required for diseases of normal tissue such as heart attack and stroke. Again, one must employ techniques such as MRS/MRI PET, and SPECT.

Previous studies have exemplified the determination of hypoxia in normal and diseased tissues by detecting metabolites of drugs named 2(2-nitro-1H-imidazol-1-yl)-N-(2,2,3,3,3-pentafluoropropyl) acetamide (hereinafter referred to as EF5) and 2(2-nitro-1H-imidazol-1-yl)-N-(3,3,3-trifluoropropyl) acetamide (hereinafter referred to as EF3). See U.S. Pat. No. 5,540,908, issued to Koch et al, the disclosures of which are herein incorporated by reference.

Notwithstanding the significant advances already attained with EF5 and EF3, there still remains a need in the art for compounds that are useful in noninvasive imaging techniques, such as MRI and PET. See also *Detection of Hypoxic Cells by Monoclonal Antibody Recognizing 2-Nitroimidazole Adducts, Cancer Res.*, 1993, 53, 5721–76, the disclosures of which are herein incorporated by reference. It is highly desirable to be able to assay for the presence of hypoxic cells in an animal or human tumor, and to do so predictably and without the concomitant hazards associated with radioactivity. The compounds and methods of the claimed invention address these, as well as other, needs in the art.

SUMMARY OF THE INVENTION

This invention presents novel nitroaromatic compounds; immunogenic conjugates comprising the novel nitroaromatic compounds and proteins; and monoclonal antibodies specific for the novel nitroaromatic compounds of the invention, their protein conjugates, their reductive byproducts, and adducts formed between mammalian hypoxic cells and the compounds of the invention. The novel compounds' protein conjugates, reductive byproducts, and adducts formed between mammalian hypoxic cells and the compounds of the invention may be generally referred to as compositions throughout this application. The novel compounds and compositions of the invention, and the methods according to this invention, provide the basis for sensitive and precise methods for detecting tissue hypoxia.

The present invention presents a novel class of compounds, structure to etanidazole but having new side chains that make them much more predictable oxygen indicators and much more amenable to immunohistochemical and other noninvasive assays. The novel compounds and compositions of the invention and the corresponding methodologies provide techniques for measuring the degree of hypoxia in mammalian tumors with a precision and sensitivity that has not been achieved before. These novel compounds and compositions may be used to detect hypoxia using standard nuclear medical procedures with a consistency not previously observed in the art. These novel compounds also provide the basis for immunological assays. These novel compounds thus afford the opportunity to study and compare their biodistribution using both microscopic (immunohistochemical) and macroscopic (immunological, MRS/MRI, PET) methods at drug concentrations appropriate for each method, but also to compare methods at constant drug concentration. This allows for much new information on the pharmacology and biodistribution of such molecules. It is seldom appreciated that drug pharmacology at drug concentrations used in typical nuclear medicine procedures, picomolar to micromolar range, may have little in common with drug pharmacology at much higher concentrations.

The novel class of compounds of this invention have the general structure depicted below

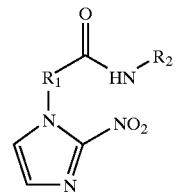

wherein $R_1$ is $CH_2$; and $R_2$ has the formula $CH_2CX_2CHX_2$, wherein X is halogen or hydrogen and at least 1 carbon atom of said $R_2$ group is substituted with at least one halogen atom.

Another aspect of the invention provides immunogenic conjugates comprising the novel compounds and a protein, and monoclonal antibodies specific for the novel compounds of the invention, their protein conjugates, reductive byproducts, and adducts formed between mammalian tissue proteins and the compounds of the invention. The protein conjugates, reductive byproducts, and adducts formed between mammalian hypoxic cells and the compounds of the invention may be referred to generally as compositions. Methods for preparing the monoclonal antibodies are also provided. As will be appreciated, the monoclonal antibodies of the invention can be either to the novel compounds per se or to the compounds bound to a protein.

In a further aspect of the invention, methods for assaying tissue hypoxia are provided. A tissue sample may be assayed using immunohistochemical techniques or imaging techniques. Imaging techniques may be used for non-invasive analysis.

Kits useful for diagnostic applications comprising the novel compounds or compositions are also within the ambit of the present invention. These kits include a drug formulation of a compound of the invention and immunochemical reagents. The compounds of the invention are very useful in detecting oxygen levels because of their dramatic specificity for hypoxic cells over normal, healthy, oxygenated tissue.

DETAILED DESCRIPTION OF PREFERRED EMBODIMENTS

Figure 1:
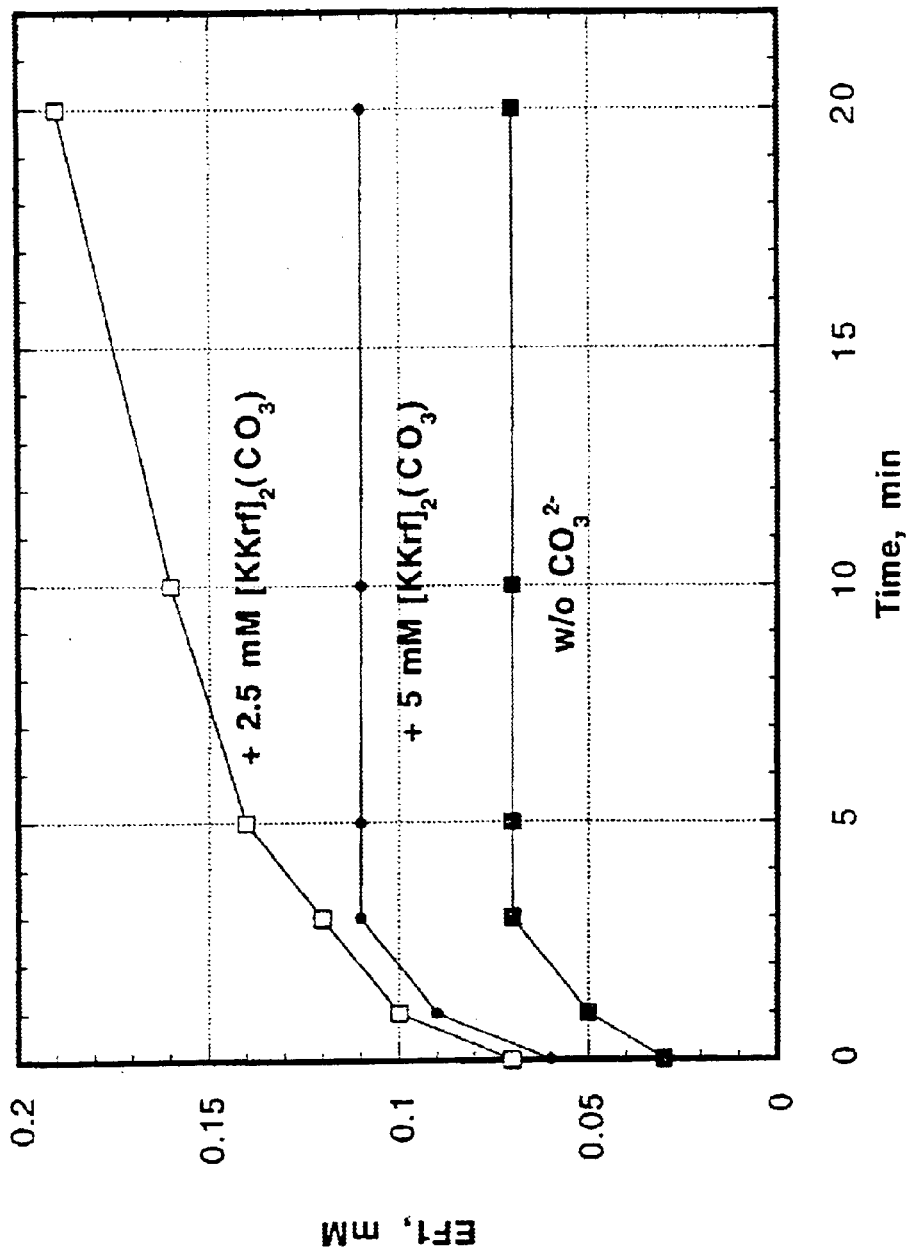
FIG. 1 illustrates the effect of carbonate ion on the kineticsj of EF1 synthesis from the mixture of Ebr1 and potassium-kryptofix fluoride in DMSO at 120° C.

The present invention provides a novel class of 2-nitroimidazole derivatives that are predictable oxygen indicators using both immunohistochemical assays and imaging techniques, said compounds having the structure:

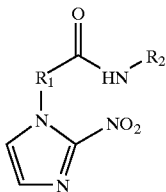

wherein $R_1$ is $CH_2$; and $R_2$ has the formula $CH_2CX_2CHX_2$, wherein X is halogen or hydrogen and at least 1 carbon atom of said $R_2$ group is substituted with at least one halogen atom.

Preferred compounds of the invention may be viewed as pairs of, for example, brominated precursor and final product. For example, in certain preferred embodiments $R_2$ is $CH_2CH_2CH_2Br$ or $CH_2CH_2CH_2F$. In other preferred embodiments, $R_2$ is $CH_2CHCHFBr$ or $CH_2CH_2CHF_2$. In yet other preferred embodiments, $R_2$ is $CH_2CF_2CH_2Br$ or $CH_2CF_2CH_2F$. And, in still other preferred embodiments, $R_2$ is $CH_2CF_2CHFBr$ or in $CH_2CF_2CHF_2$. Also, in certain preferred embodiments where non-invasive imaging is used, one of the halogen atoms may be radioactive fluorine ($^{18}F$), having arisen from a precursor with bromine.

It is also believed to be possible to add fluorine gas across a double bond between the second and terminal carbon, leading to the possibility of only a single fluorine at the second carbon. Thus, in still other preferred embodiments, $R_2$ is $CH_2CHFCH_2F$, $CH_2CHFCHF_2$.

Because of the inherent difficulties in fluorine chemistry and exchange reactions it may be that other precursor molecules and final products of the general type specified may be most efficacious. It is believed that all molecules of this sort will have similar oxygen detection characteristics, the optimal compound is likely to be that which has the greatest efficiency of synthesis in radioactive form. Such compounds are contemplated to be within the scope of the claimed invention.

This invention is further directed to drug-protein conjugates (immunogenic conjugates) formed between a compound of the invention and a suitable carrier protein, these compositions may be referred to as antigens in this application. Proteins suitable for practicing this aspect of the invention include, without limitation, albumin, lysozyme (LYZ), or Bowman Birk inhibitor (BBI). In certain preferred embodiments, the immunogenic conjugates may have an $R_2$ as described above together with BBI. For example, $R_2$ may be $CH_2CF_2CH_2F$; $CH_2CH_2CH_2Y$; or $CH_2CF_2CHF_2$.

The invention also presents methods for preparing a monoclonal antibody, which comprises introducing into a mammal a protein conjugate of the invention; fusing immune cells of the mammal with mammalian myeloma cells forming a hybridoma that produces antibodies specific for the compound bound to the protein. Monoclonal antibodies are also within the ambit of this invention.

In certain preferred embodiments, the protein is albumin, lysozyme, or Bowman Birk inhibitor and $R_2$ may be $CH_2CF_2CH_2F$; $CH_2CH_2CH_2F$; or $CH_2CF_2CHF_2$.

In one preferred embodiment of the invention, monoclonal antibodies will be specific for compounds and compositions of the invention where the halogen atom(s) are fluorine.

Methods for detecting tissue hypoxia are also presented. Imaging methods comprise using the novel compounds of the invention with or without immunohistochemical assays, preferably without the use of monoclonal antibodies to detect hypoxic cells.

In a noninvasive assay, the mammal is administered a compound of the invention, dissolved or dispersed in a suitable pharmaceutical carrier or diluent such as non-pyrogenic physiological saline. Any such diluents known to those skilled in the art may be used without departing from the spirit of the invention. The compound is allowed to partially clear from the mammal and to be taken up preferentially through the bioreductive metabolism of hypoxic cells, and then a portion of the mammal containing the tissue of interest is analyzed non-invasively such as through magnetic resonance imaging (MRI) or positron emission tomography (PET). A proportion of the compound will remain in the body, bound or associated with hypoxic cells. Tissue hypoxia is assayed using detectors of the marker atoms. Tissue hypoxia is assayed using detectors of the marker atoms. In the case of MRI, conventional non-radioactive ($^{18}F$) isotopes of fluorine are used. In the case of PET, a compound of the invention must first be formulated with the positron emitting isotope $^{18}F$. Because of the short half-life of radioactive fluorine (110 min) a compromise must be reached between having the maximum clearance providing the best signal: noise ratio), and having enough signal to provide adequate image resolution.

Imaging techniques suitable for practicing the invention include, but are not limited to, single photon emission computed tomography (SPECT), PET, and nuclear magnetic resonance imaging, usually called MRI. Generally, imaging techniques involve administering a compound with marker atoms that can be detected externally to the mammal.

Particularly preferred imaging methods for practicing the claimed invention include, PET, SPECT, or MRI. When the detection technique is PET, it is preferred that $R_2$ is $CH_2CH_2CH_2{}^{18}F$. When the detection technique is MRI, it is preferred that $R_2$ is $CH_2CH_2CH_2{}^{19}F$. In certain preferred methods, the label is a positron or gamma emitting isotope.

In another embodiment of the invention, the assay methods use immunochemistry. Generally, immnunohistochemistry involves staining cryosectioned tissue samples. These methods generally comprise administering to a mammal, as above, a compound of the invention; obtaining a tissue sample; and detecting the presence of adducts formed between cells of the sample and a compound of the invention by contacting the tissue sample with the invention's monoclonal antibodies associated with a detection system. The mAb will be specific for the adduct; that is, the mAb will be specific for the adduct formed between tissue proteins and the compound previously administered. In other words, the compound selectively binds to the tissue proteins of hypoxic cells to form an adduct. A sample of tumor tissue is obtained and the degree of tissue hypoxia is determined by quantifying the level of antibody interaction with the cells such as by using enzyme linked immunosorbant assay (ELISA), microdialysis, immunohistochemical staining, or other immunological protocols. The degree of binding of the antibodies to the side chain of the adduct provides a measurement of the degree of hypoxia in the tumor tissue. In a preferred embodiment of the invention, the monoclonal antibodies of the invention can be used with cells or tissue sections fixed in paraformaldehyde.

Methods of obtaining tissue samples for analysis, include any surgical and nonsurgical technique known in the art. Surgical methods include, but are not limited to biopsy such as fine needle aspirate, core biopsy, dilation and curettage.

Immunohistological techniques suitable for practicing the invention include, without limitation, immunoblotting or Western blotting, ELISA, sandwich assays, fluorescence, biotin or enzymatic labeling with or without secondary antibodies.

In certain preferred embodiments, $R_2$ is $CH_2CH_2CH_2Br$ or $CH_2CH_2CH_2F$. In other preferred embodiments, $R_2$ is $CH_2CH_2CHFBr$ or $CH_2CH_2CHF_2$. In yet other preferred embodiments, $R_2$ is $CH_2CF_2CH_2Br$ or $CH_2CF_2CH_2F$. And, in still other preferred embodiments, $R_2$ is $CH_2CF_2CHFBr$ or $CH_2CF_2CHF_2$. In still other preferred embodiments, $R_2$ is $CH_2CHFCH_2F$, $CH_2CHFCHF_2$. In certain preferred embodiments, the isotope is $^{18}F$.

For purposes of the current invention, mammals include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids humans and apes). The preferred mammals are humans.

The invention is further directed to pharmaceutical formulations of the novel drug compounds. In accordance with preferred embodiments, a compound of the invention is dissolved or dispersed in a pharmaceutically acceptable diluent. Preferred diluents are non-pyrogenic physiological saline.

The invention is also directed to formulations of immunogenic conjugates comprising the novel drug compounds of the invention bound to a protein carrier and dissolved or dispersed in a diluent.

Diagnostic kits are also within the scope of this invention. Such kits may include monoclonal antibodies that can rapidly detect tissue hypoxia; and include a compound of the invention, individual or mixed monoclonal antibodies against adducts formed between a compound of the invention and tissue proteins; and detection moieties. Preferably, standards of manufactured protein adducts to be used as calibration sources for the assays are also included.

Due to the unusual chemical properties of the novel claimed multiply halogenated alkyl chains, new chemical methods were used to synthesize the claimed compounds because previous work done to produce molecules suitable for PET imaging have not involved structures of this type. In particular, the degree of halogen saturation on the terminal carbon was modified to allow fluorine for bromine substitution while minimizing bromine elimination and/or molecular destruction under conditions suitable for such substitution (hot DMSO with fluoride carrier). The modifications allow the production of EF5 analogs with sidechains ending in $-CH_2CHF$, $-CH_2CHF_2$, $-CHFCH_2F$, $-CHFCHF_2$, $-CF_2CH_2F$ and $-CF_2CHF_2$. In each case, the brominated precursor molecule will have one of the terminal fluorines substituted by bromine.

Generally, the compounds of the invention can be synthesized using various reaction conditions depending on the starring material and ultimate requirements. In general there are up to 4 steps of the synthesis. First, the staring material for all compounds can be 2-nitroimidazol-1[H]-yl)-acetic acid. The terminal part of the side chain, containing the $R_2$ group as specified above, is a derivative of propylamine, wherein the $C_2$ and $C_3$ position are modified to contain one or more bromines and/or fluorines, in the next step. In the third step, the substituted propylamine is conjugated to the 2-nitroimidazol-1[H]-yl)-acetic acid in a mixed anhydride reaction. A final step may include the radioactive fluorine for bromine exchange reaction to make an agent suitable for PET imaging. Making of PET isotope-containing derivatives requires rapid addition of the $^{18}F$ moiety followed by immediate purification and use because of the short half-life of $^{18}F$, 109.7 minutes.

Generally, the third step of the synthesis for compounds of the invention is performed under the following reaction conditions. The reaction may be performed in anhydrous aprotic solvent with low boiling point (tetrahydrofuran or acetonitrile) under argon in the presence of tertiary amine (N-methylmorpholine or triethylamine) by addition of isobutylchloroformate. The acid derivative then undergoes nucleophilic substitution with a halogenated alkylamine at the acid's carbonyl group to yield a halogenated nitroimidazole acetamide. Other synthetic methods will be apparent to those skilled in the art and may be used without departing from the spirit of the invention.

The claimed novel sidechains of the invention may generally be fluorine derivatives of propylamine. It is contemplated that these novel sidechains may be introduced into other compositions and compounds other than 2-nitroimidazole acetamide, including, without limitation, antibodies, receptors, protein conjugates, and the like. To make such compounds or compositions PET agents, OFF is introduced into analogous compounds with bromine instead of fluorine. Generally, such a method would include conjugating a propylamine-based side chain with a carboxyl group of the compound or composition of interest ($R_3COOH$), forming $R_3CONHR_2$, where $R_2$ may be $CH_2CX_2CHX_2$. The next step is the introducing of $^{18}F$ by the exchange with bromine, as described, for example, in example 10. Any such compounds or compositions containing the novel sidechains of the invention are contemplated to be within the scope of the invention, as are the methods for making the same.

The reaction may yield a reaction slurry from which the product must be recovered. Methods of recovering the sample include any filtration or separation techniques known in the art. Such methods include, but are not limited to, vacuum filtration, separatory extraction, or distillation. A preferred method is filtration using air or liquid, but other methods will be apparent to those skilled in the art.

The filtration solid may further require washing with organic solvents to separate out impurities or other reaction intermediates or byproducts. Organic solvents include, but are not limited to, ether, methanol, ethanol, ethyl acetate, or hexanes. Ether is a preferred solvent, but other types of solvents will be apparent to those skilled in the art. Any organic solvent should be evaporated using methods known in the art. Evaporation methods may be accomplished at room temperature, by vacuum, aspiration, or by using latent heat. The evaporation methods are not limited to these techniques and other techniques will be apparent to those skilled in the art.

The reaction product is then purified using purification techniques known in the art. These techniques include, but are not limited to, column chromatography, flash chromatography, recrystillization, or gel chromatography. When using chromatographic purification methods, gradient elution is preferred. Combinations of organic solvents include, but are not limited to, methanol, acetonitrile, hexanes, carbon tetrachloride, and ethyl acetate. Other purification methods will be apparent to those skilled in the art.

This invention is further directed to drug-protein conjugates formed between a compound of the invention and a suitable carrier protein, these compositions are referred to as antigens throughout this application. Antigens prepared using technology known in the art did not produce active mAbs, so previous procedures were substantially modified.

The prior art relates that antigen-forming reactions may be carried out between pH 4 to 7. It has now been found that these conditions fail to produce a sufficient number of drug-protein conjugates. It is greatly preferred to carry out the antigen-forming reactions at neutral or higher pH, preferably near neutrality. Under these conditions the drug-protein conjugation is much more efficient.

The conjugation process is also much more efficient when the carrier protein contains cysteine sulfhydryl groups (PSH). Unfortunately, the cysteine residues of most proteins are a) few in number (e.g., hemocyanin); b) are not accessible (e.g., alcohol dehydrogenase); or c) are oxidized as cystine diners which do not bind reduced nitroaromatics. Although cystine dimers of several proteins can be very efficiently reduced via a radiochemical chain reaction, Koch & Raleigh, *Arch. Biochem. Biophys.*, 1991,287, 75, the resulting modified protein is often insoluble possibly because of the formation of disulfide bridges between molecules. It was not possible to reduce the protein cystines by addition of excess quantities of agents such as dithiothreitol or mercaptoethanol, which can simultaneously reduce and stabilize cystine-containing proteins, because then adducts would preferentially form with the excess low-molecular weight thiol. Thus it was convenient to identify a protein with high cystine content, and having relative freedom from precipitation on radiochemical reduction. Bowman Birk Inhibitor, a trypsin/chymotrypsin inhibitor from soybeans, (Bowrman Birk Inhibitor (BBI)—7 cystine bridges, molecular mass 7800) was found to have near optimal characteristics from this point of view, and reduction of up to an average of 8 cysteine residues was possible. The EF5-BBI conjugates were then made in a second radiochemical reduction step. Oxygen is excluded from the solutions using techniques previously described in Koch & Raleigh, *Arch Biochem. Biophys.*, supra. Glass containers with specially constructed ceramic-enclosed spin bars to eliminate oxygen released from Teflon, Franko, et al., *"Recent Results in Cancer Res. 95" in Culture of Cellular Spheroids* 62 (Verlag 1984), were placed into leak proof aluminum chambers, and the oxygen-containing air was replaced by nitrogen using a number of gas exchanges.

The monoclonal antibodies of the invention may be synthesized using the drug-protein conjugate of the invention. These conjugates are prepared according to the aforementioned procedure and are used to elicit antibody formation. When a drug-protein conjugate of the invention is bound to a protein carrier in vitro and administered to a mammal, monoclonal antibodies specific for compounds of the invention, their protein conjugates, reductive byproducts, and adducts formed between mammalian hypoxic cells and the compounds of the invention can be raised. The preparation of monoclonal antibodies is known in the art. Particularly, Kohier and Milstein's method, Kohler, et al., *Nature*, 1975, 256, 495, with modifications as described in Knauf, et al., *Cancer Immunol. Immunotherapy*, 1986, 21, 217–225.

Generally, drug-protein conjugate compositions would be used to immunize mice using conventional techniques. See generally Knauf, et al., supra. A host is injected with a drug-protein conjugate of the invention, serving as antigen to elicit an immune response. After an appropriate incubation period, blood would be drained from the host and analyzed. If the host's serum shows strong activity against the antigen, the animal would be sacrificed and its spleen cells used to make hybridoma clones. Kohler, et al., supra. Such hybridomas are capable of producing monoclonal antibodies specific for the drug of the particular drug-protein conjugate administered to the mammal. Kohler, et al., supra. In a preferred embodiment of the invention, the hybridoma clone will be conditioned to grow in serum-free medium.

This ability to grow in serum-free medium permits facile purification of the antibodies and the easy addition of detection moieties as a fluorophore, biotin, or an enzyme.

The drug compounds of the invention are very useful in detecting oxygen levels because of their dramatic specificity for hypoxic cells over normal healthy oxygenated tissue. For example, when hypoxic cells and aerobic cells are incubated in the presence of the new novel compounds, the monoclonal antibodies of the invention selectively bind to hypoxic cells. This preferential binding provides the basis for assaying tissues in mammals using immunohistological techniques.

The compounds of the invention possess unique properties that make them safer and more predictable oxygen indicators than previous compounds. The structure of the parent 2-nitroimidazole, etanidazole, N-(2-hydroxyethyl)-2 (2-nitro-1H-imidazol-1-yl) acetamide, has been shown to be less susceptible to non-oxygen-dependent variations in adduct formation than is misonidazole. Also, the increased solubility of the compounds of the invention over misonidazole derivatives currently in use permits administering a higher drug concentration resulting in enhanced detection sensitivity without the toxicity observed with current methods.

It is believed that because the side chains of the claimed compounds of are highly non-physiological they will exhibit good antigenic characteristics. Monoclonal antibodies of this invention would be specific for the novel nitroaromatic compounds of the, invention, their protein conjugates, their reductive byproducts, and adducts formed between mammalian hypoxic cells and the compounds of the invention. This specificity would make these antibodies superior detectors than the polyclonal antibodies currently used in the art. As indicated above, a consistent source of identical antibodies is required for clinical assays. The novel compounds of the invention provide the basis for a sensitive, versatile, and more accurate method for detecting tissue hypoxia.

Preferred aspects of the invention are discussed in the following examples. While the present invention has been described with specificity in accordance with certain of its preferred embodiments, the invention is not so limited.

EXAMPLE 1

Synthesis of 2,2,3,3-pentafluoropropylamine (for Making EF5)

Obtained commercially (PCR, Inc., P.O. Box 1466, Gainesille, Fla. 32602)

EXAMPLE 2

Synthesis of 3-bromo-2,2,3,3-tetrafluoropropylamine 3-bromo-2,2,3,3-tetrafluoropropylamine was prepared through the intermediate of 4-bromo-4,4,3,3-tetrafluorobutanoic acid (from literature: Wei Yuan, R, Long, L., and Yuan-Fa, Z, *Chinese J. Chemistry* 1990, 3, 281). The reactions can be described by the following scheme:

$Na_2S_2O_4/NaHCO_3$ in $CH_3CN/H_2O$ $BrCF_2CF_2Br+CH_2=CHOEt \rightarrow BrCF_2CF_2CH_2CHBrOEt$ $CrO_3/H_2SO_4$ in $CH_3COCH_3$, $NaN_3/H_2SO_4$; $HCl \rightarrow BrCF_2CF_2CH_2COOH \rightarrow BrCF_2CF_2NH_3Cl$ $BrCF_2CF_2COOH$ (1.2 g, 5 mmol) was dissolved in 3 ml of $H_2SO_4$. Sodium azide (0.8 g, 12 mmol) was added in portion to the mixture at 80°. After addition was completed the reaction was continued for 20 hr. The mixture was then cooled to 0°. The solution was diluted with dichloromethane and then sodium carbonate (4 g in 20 ml of water). The organic layer was separated and the water layer was extracted with $CH_2Cl_2$ (20 ml×2). The combined dichloromethane was dried over magnesium sulfate overnight and gaseous HCl bubbled into the solution. 0.79 g of white solid was collected by filtration and vacuum dried. $^1$H NMR δ 3.82 (t, J=16 Hz, 2H). $^{19}$F NMR δ −66.8 (t, J=16 Hz, 2H), −113.74 (m, 2F). Chemical analysis: Calculated for $C_3H_5BrClF_4BN$ C: 14.6, H: 2.03, N:5.68. Found C: 14.57, H: 1.96, N: 5.56.

EXAMPLE 3

Synthesis of 3,3,3-trifluoropropylamine (for Making EF3)

3,3,3-trifluoropropylamine hydrofluoride can be prepared in one step by treatment of 3-aminopropionic acid with excess $SF_4$ in anhydrous HF at 180° C. The product can be converted to the hydrochloride by subsequent treatment with 40% KOH followed by an excess of HCl.

EXAMPLE 4

Synthesis of 3-bromo-3,3-difluoropropylamine 3-bromo-3,3-difluoropropylamine was prepared through the intermediate of 3-bromo-3,3-difluoropropylazide according to the following, reaction schemes:

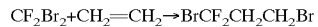

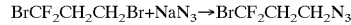

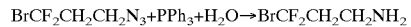

3-bromo-3,3-difluoropropylazide was made by adding sodium azide (5 g, 77 mmol) and 1,3-dibromo-1,1-difluoropropane (12 g, 50 mmol) in 50 ml DMSO. The mixture was stirred for 6 h at room temperature. After purification, 6.3 g of product was obtained. $^1$H NMR δ 2.59 (m, 2H), 3.51 (t, J=7 Hz, 2H). $^{19}$F NMR δ −49.07 (t,=12 Hz, 2F). HRMS for $C_3H_4F_2N3$ Calc. 198.9557,200.9537. Found 198.9555, 200.9523.

Then, 3-bromo-3,3-difluoropropylamine was made by combining triphenylphosphine (2.62 g, 10 mmol), THF (10 ml) and water (1 ml) in a 50 ml round bottom flask 3-bromo-3,3-difluoropropylazide (1 g, 5 mmol) was added dropwise to The mixture at 0°. After addition, the mixture was allowed to stir for an additional 6 hours. The product in THF was obtained by vacuum transfer. Most of the THF was removed by rotary evaporation. The residue was diluted by diethylether, and the ether layer dried over magnesium sulfate overnight. To prepare the hydrochloride, HCl was bubbled into the solution. The white solid (0.21 g) was obtained after filtration and vacuum dried.

$^1$H NMR δ 2.80 (m, 2H), 3.23 (t, J=7 Hz, 2H). $^{19}$F NMR δ −43.13 (t, J=12 Hz, 2F). Anal. Calcd. for $C_3H_7BrClF_2N$ C:17.1 H: 3.33 N: 6.65. Found C:17.12 H: 3.23 N: 6.48.

EXAMPLE 5

Synthesis of 3,3-difluoropropylamine

Synthesis of this compound uses 3-bromo-3,3 difluoropopylazide (described above) as starting material. 5 g (2.5 mmol) of 3-bromo-3,3 difluoropopylazide was added to benzene (10 ml) under nitrogen in combination with tributyltin hydride (2.91 g, 10 mmol). The mixture was refluxed for 8 h. The product went with benzene by vacuum transfer and following bubbling with HCl a white precipitate appeared. This was filtered and dried under vacuum to provide the final compound (0.51 g). $^1$H NMR δ 2.20 (m, 2H), 3.13 (t, J=7 Hz, 2H), 6.03 (t of t, J=56 Hz, J=41 Hz, 1H). $^{19}$F NMR δ −115.52 (d of t, J=56 Hz, J=18 Hz, 2F). Anal. Calcd for $C_3H_8BrClF_2N$ C:27.38 H: 6.08 N: 10.65. Found C: 27.45 H: 6.31 N: 10.42.

EXAMPLE 6

Synthesis of 3-fluoropropylamine 3-fluoropropylamine hydrochloride was prepared through the intermediate 3-fluoropropylazide according to the following reaction scheme:

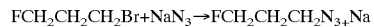

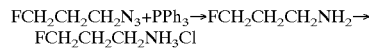

Sodium azide (1 g, 15 mmol) was stirred at room temperature with 15 mL of DMSO until most of sodium azide was dissolved. Then $FCH_2CH_2CH_2Br$ (1.41 g, 10 mmol) was added to the mixture and continued stirring for 6 hours. The crude product (0.85 g, 83%) was obtained by vacuum transfer. $^1$H NMR δ 1.23 (m, 2H), 2.72 (t, J=7 Hz, 2H), 3.93 (d of t, J=47 Hz, J=6 Hz, 2H). $^{19}$F NMR δ −222.80 (m, 1F).

Triphenylphosphine (2.62 g, 10 mmol) was dissolved in 8 mL of THF, then 3-fluoropropylazide (0.85 g. 8.3 mmol) was added dropwise to the solution at 0° C. After addition, the mixture was warmed to room temperature slowly and stirred for an additional 6 hours, then water (0.22 g, 12 mmol) was added to the solution. The mixture was stirred at room temperature overnight. The product in THF was obtained by vacuum transfer and was acidified with dry hydrogen chloride. The white precipitate was filtered to provide 0.63 g (48%) of product. $^1$H NMR d 1.95 (m, 2H), 3.04 (t, J=7 Hz, 2H), 4.50 (d of t, J=47 Hz, J=5 Hz, 2H). $^{19}$F NMR d −219.70 (m, 1F). Analysis: calculated for $C_3H_9ClFN$ C:31.72, H: 7.93, N 12.33; found C:31.56, H: 8.20, N 11.83.

EXAMPLE 7

Synthesis of 3-bromo-2,2-difluoropropylamine

The reaction scheme is analogous to the synthesis of 3-bromo-2,2,3,3-tetrafluoropropylamine (see Example 2). In this synthesis $BrCF_2CH_2Br$ is using as a starting material instead of $BrCF_2CF_2Br$, leading to synthesis of $BrCH_2CF_2CH_2COOH$ after oxidation of addition product by chromium (VI) oxide and $BrCH_2CF_2CH_2NH_3Cl$ after sodium azide treatment.

EXAMPLE 8

Synthesis of 3-bromopropylamine (for Making Ebr1)

Obtained commercially (Aldrich).

EXAMPLE 9

Optimization of the Synthesis of EF1 from EBr1

EF1 was prepared from EBr1 by the direct exchange of bromine with potassium-kryptofix [2,2,2] fluoride in DMSO. In typical preparation 100 μL of water, containing 7 μmol of potassium-kryptofix [2,2,2] fluoride and 1.5 μmol of potassium-kryptofix [2,2,2] carbonate were dried by azeotropic distillation with acetonitrile (3¥2 mL) at 120° C. under stream of argon. Solution of 2.9 mg EBr1 (10 μM) in 1 mL of DMSO was added and the mixture was heated at 120° C. for 40 min under nitrogen. The probes of solution were diluted 1:100 into 0.1 M ammonia-acetate buffer and analyzed by HPLC on C-18 column with elution by the same buffer with 10% methanol and detection of absorbency at 325 nm (for 2-nitroimidazole e=7,500). Comparison of HPLC data with standard solution shows the yield of EF1 approximately 2%, which may be considered acceptable for preparation of [$^{18}$F]-EF1.

To optimize the reaction conditions, the reaction conditions were varied. Addition of 10-fold excess of fluoride to any 2-nitroimidazole derivative at room temperature caused a rapid change of yellowish color of solution to dark-blue and next brown. Absorption spectrum of product has no band at 325 nm, suggestion the decomposition of 2-nitroimidazole ring. Accordingly, an excess of fluoride can not be used for the reaction.

Presence of traces of water drastically reduced the yield of EF1 and causes a production of subsequent hydroxyl derivative. In order to prevent this effect, the anhydrous DMSO was preheated before the reaction at 120° C. with bubbling of argon during 2 hours.

Preparation of [$^{18}$F] (see below) implies the presence of residual carbonate in solution. The effect of carbonate on the reaction kinetics was determined. The results (FIG. 4) show, that optimal ratio of fluoride to carbonate is 4:1, which is consistent with data. Hamacher, et al, *J. Nuc. Med*, 1986, 27, 238. Efficient stereospecific synthesis of no-carrier-added 2-[$^{18}$F]-fluoro-2-deoxy-D-glucose using aminopolyether supported nucleophilic substitution.

Different aprotic solvents were tested. The yield of EF1 was negligible in hexamethylphosphamide, 0.2% in dimethylformamide and 0.8% in dimethyliraidazolinone. Subsequently, DMSO (2%) is the optimal solvent for the reaction, probably due to the most efficient ionization of F in solution.

EXAMPLE 10

Preparation of [$^{18}$F]-EF1

[$^{18}$F]-hydrofluoric acid was prepared by the $^{18}$O(p,n)$^{18}$F reaction using enriched water as the target material. The [$^{18}$F]-hydrofluoric acid (200 mCi) was mixed with 100 μL of water, containing 7 μmol of potassium-Kryptofix [2,2,2] fluoride and 1.5 μmol of potassium-Kryptofix [2,2,2] carbonate. The solution was dried by azeotropic distillation with acetonitrile (3¥2 mL) at 120° C., and solution of 2.9 mg EBr1 (10 μM) in 0.5 mL of DMSO was added. The solution was heated at 120° C. for 40 min under nitrogen. The reaction vessel was cooled and 3 mL of water was added. In order to remove unreacted fluoride, the water solution was passed through the column, packed with Dowex 1X4-50 chloride. The yield of radioactive product was 1.5 mCi.

Figure 2:
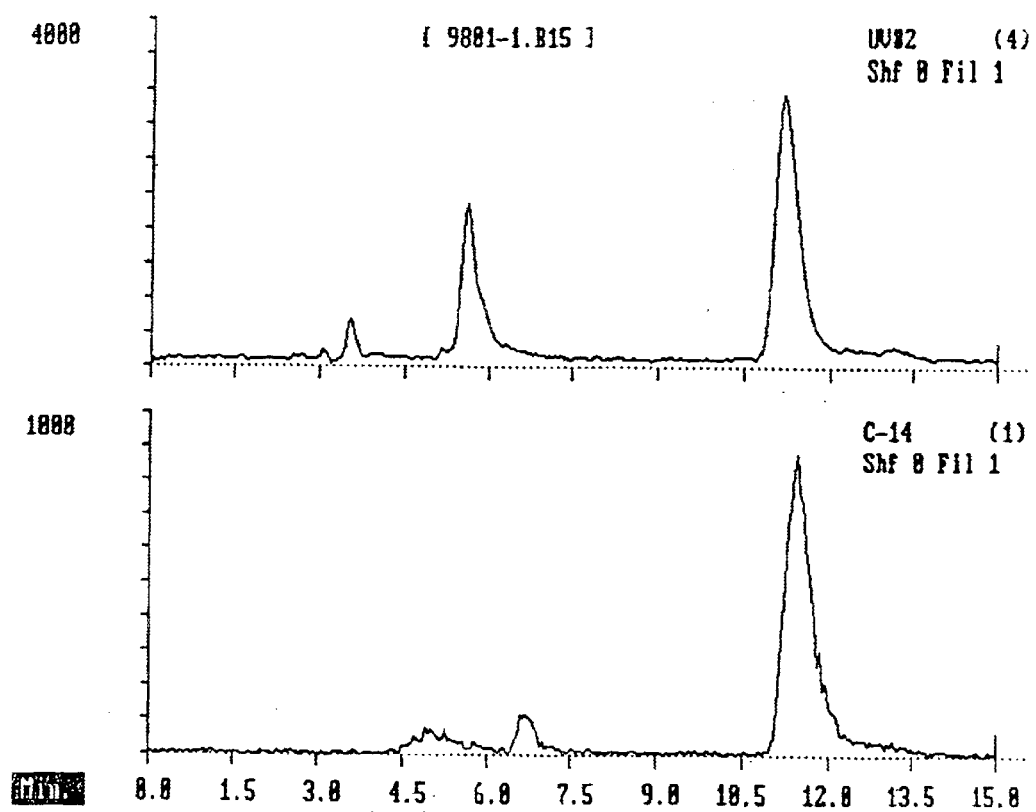
FIG. 2 represents the HPLC analysis of the product of EF1 synthesis in the presence of radioactive $^{18}F$ with simultaneous detection of absorbency at 325 nm (upper curve) and radioactivity (lower curve); peak at 11–12 min. represents EBF.

The probe of solution was analyzed by HPLC with simultaneous detection of 325 nm absorbency and radioactivity. As seen in FIG. 2, most of radioactivity is eluted as a single peak, correspondent to 325 nm absorbency peak of EF1. Subsequently, the solution contains $^{18}$F mostly in the form of [$^{18}$F]-EF1.

Figure 3:
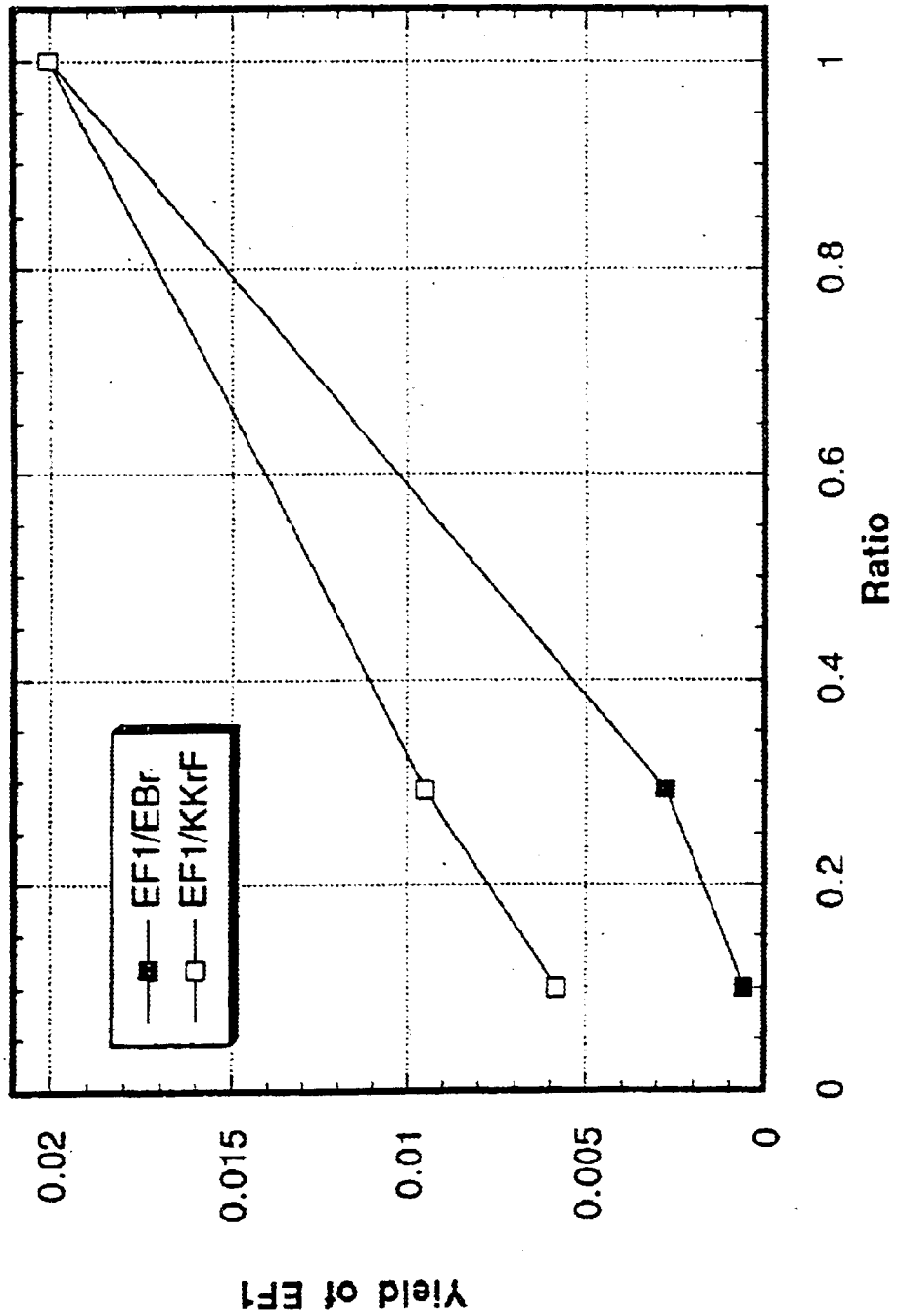
FIG. 3 depicts the effect of relative flouride concentration on the EF1 yield.

The described above procedure involves the addition of carrier $^{19}$F to the reaction mixture. It seems to be more logical to use only radioactive fluoride to achieve higher degree of conversion of $^{18}$F into [$^{18}$F]-EF1. However, attempts to use only $^{18}$F without carrier resulted in the very low (if any) production of [$^{18}$F]-EF1. To explain this effect, the reaction was performed at fixed EBr1 concentration, decreasing the F-/EBr1 ratio. As it is shown in FIG. 3, it also caused the decrease of the relative yield of EF1, as compared with fluoride. Subsequently, the decrease of fluoride concentration does not favor the conversion of fluoride into EF1, probably due to overwhelming by other reactions. Another explanation on the necessity of the carrier is very low concentration of $^{18}$F in solution. High specific activity (1.71·10$^9$ Ci/mmol) suggests the 6·10$^{-13}$ M concentration of fluoride in the reaction solution At this low concentration the traces of water and other impurities may significantly affect the reaction, causing decrease of the [$^{18}$F]-EF1 yield.

EXAMPLE 11

PET Analysis of a Tumor-bearing Rat Treated with [$^{18}$F]-EF1

Figure 4:
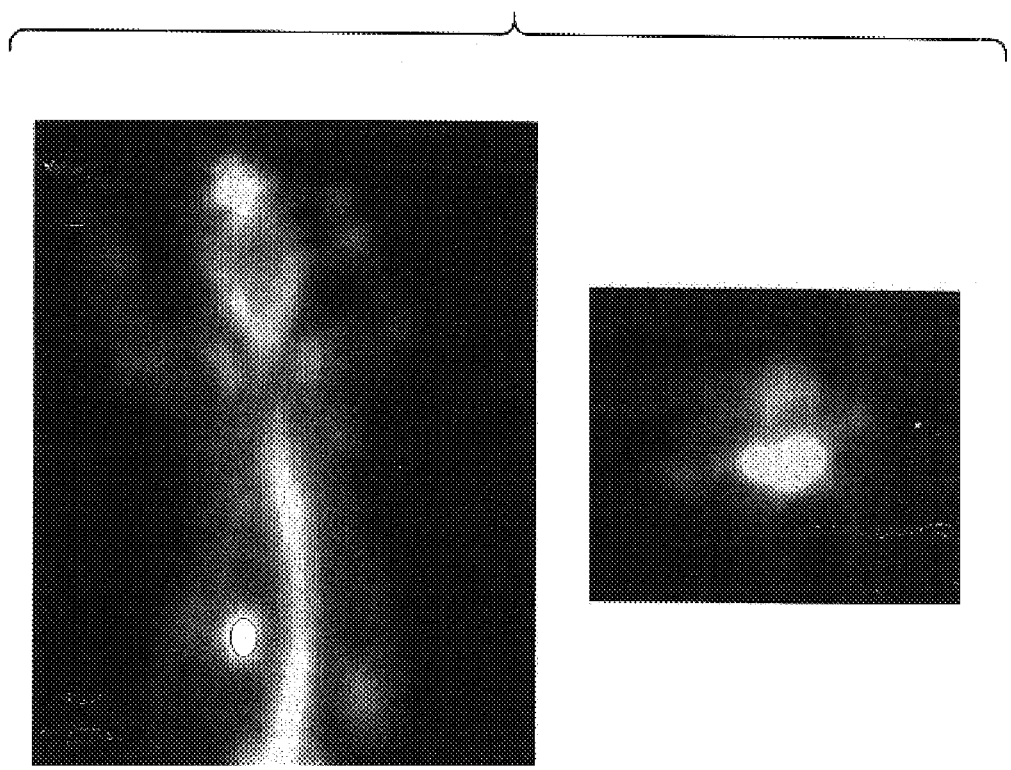
FIG. 4 illustrates a PET image of a tumor-bearing rat treated with 18-F-labeled EF1 (2-(2-nitro-1H-imidazol-1-yl)-N-3-monofluoropropyl) acetamide, 150 minutes post injection.

FIG. 4 illustrates a PET image of a tumor-bearing rat treated with 18-F-labeled EF1 (2-(2-nitro-1H-imidazol-1-yl)-N-3-monofluoropropyl) acetamide, 150 minutes post injection.

Q7 cells were obtained from the American Type Culture Collection (ATCC). They were maintained in exponential growth by transfers at 3.5 day intervals with standard culture conditions. Growth medium was Eagle's MEM supplemented with 15% fetal calf serum and standard penicillin and streptomycin.

All animal studies conformed to the regulations of the University of Pennsylvania Institutional Animal Care and Use Committee. Male Buffalo rats (Harlan Sprague Dawley, Indianapolis, Ind., USA) were used for all studies. Donor tumors were created by injecting 1 million Q7 cells subcutaneously into the thigh region. The average growth time to achieve a 1 cm diameter tumor was 21 days. Tumors of less than 2 g were used in the experiments.

The tumor (Morris 7777 hepatoma)is clearly visible even though various organs also expected to bind the drug were nearby (liver, kidney, stomach, cecum, digestive track etc.). It is believed that this is the first PET image of a rodent tumor where substantial image modifications to eliminate gut clearance effects have not been necessary.

EXAMPLE 12

Figure 5:
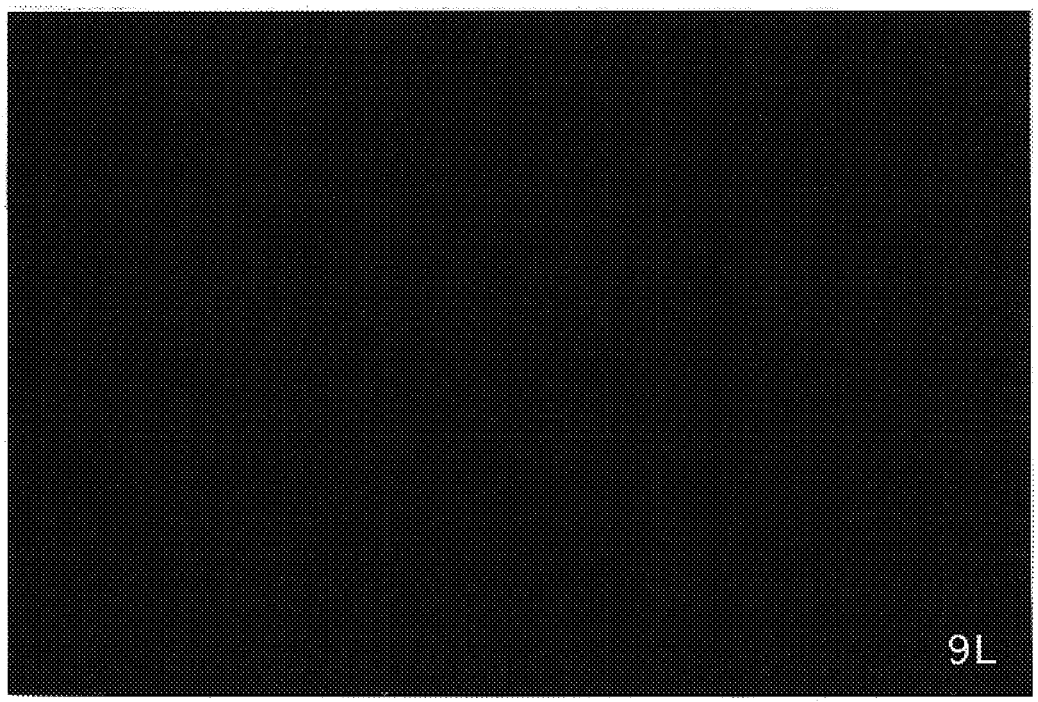
FIG. 5 depicts a typical tissue section from the tumor of FIG. 4 stained with anti-EF3 antibodies and imaged by fluorescence microscopy as previously described.: See Evans et. al, *Brit J. Cancer*, 1995, 72, 875–882.

Analysis of Tissue Section from the Tumor of FIG. 4 Stained with Anti-EF3 Antibodies and Imaged by Fluorescence Microscopy FIG. 5 depicts a typical tissue section from the tumor of FIG. 4 stained with anti-EF3 antibodies and imaged by fluorescence microscopy as previously described. See Evans et al, *Brit J. Cancer*, 1995, 72, 875–882. Since existing antibodies (to EF5 and EF3) have only a modest affinity towards EF1, the rat was simultaneously injected with EF3 to allow normal immunohistochemical staining of the tumor tissue. Q7 tumor sections were cut at 14 μm thickness using a Microm HM 505N cryostat and collected onto poly-L-tysine coated microscope slides. The sections were fixed for one hour in ice cold Dulbecco's phosphate-buffered saline (1×PBS) containing freshly dissolved paraformaldehyde (4%m, pH 7.1–7.4, SIGMA P-6148). The rinsing, blocking and staining of tissue sections for EF3 binding was identical to that described previously.

EF3 binding was assessed by imaging the tissue sections at the appropriate wavelengths for EUL5-A8 (535 nm excitation, 605 nm emission). Slides were imaged using a Nikon fluorescence microscope fitted with either a standard camera back (for Ektachrome. Elite 400 film) or digital CCD camera (Xillix Technologies, Vancouver). Preceding microscope use, the brightness of the fluorescent bulb was calibrated so that measurements of exposure times for individual tissue sections could be directly compared. EUL5-A8 dye with absorbency 1.25 at 549 nm was loaded into a hemcytometer and the fluorescence recorded after focusing the microscope on the ruled grid of the hemocytometer. Image fields of 1.2 mm×1.0 mm and 1.05 mm×0.75 mm were obtained from the CCD and regular camera, respectively, for a 10× objective, and correspondingly larger fields for a 4× objective. Photography of EUL5-A8 conjugated antibody was made at noted vernier locations on the tissue section.

EXAMPLE 13

Analysis of the Distribution of Radioactive Drug in Various Organs and Tissues

To measure the distribution of radioactive drug in various organs and tissues, the solution of [$^{18}$F]-EF1 in saline buffer was injected I/V into 2 male Buffalo rats. Animals was sacrificed and the samples of tissues were collected and weighted. The radioactivity of samples was measured by γ-counter and corrected for weight and the time of decay.

Table 1 shows the actual distribution of radioactive counts from various organs and tissues after animal sacrifice and tissue collection. In particular, note that the density of radioactive counts closely parallels the findings from the image analysis. Results from 2 animals, are shown. PET and immunohistochemical images from both animals were very similar (data not shown)

TABLE 1

Tissue distribution of [$^{18}$F]-EF1 in rats bearing tumors (% dose/gram).

| Organ | 3 hrs | 3 hrs | 4 hrs | 4 hrs |
|---|---|---|---|---|
| Blood | 0.31 | 0.12 | — | — |
| Brain | 0.13 | 0.11 | — | — |
| Liver | 0.25 | 0.21 | 0.41 | 0.19 |
| Spleen | 0.17 | 0.13 | 0.36 | 0.15 |
| Kidney | 0.54 | 0.29 | 0.67 | 0.31 |
| Muscle | 0.17 | 0.13 | 0.23 | 0.13 |
| Tumor | 0.34 | 0.28 | 0.64 | 0.44 |

EXAMPLE 14

Analysis of the Distribution of Radioactive Drug in Various Murine Organs and Tissues The distribution of radioactive drug in various murine organs and tissues was measured similarly to the previous example. [$^{18}$F]-EF1 was injected into 4 mice, which were sacrificed after 5 and 90 minutes and the radioactivity of tissues was measured.

Table 2 shows the biodistribution of EF1 in various murine tissues at varying times after drug administration. The overall distribution of counts is quite similar to that found for radioactive EF5($^{14}$C-labeled) except for brain. Mouse-brain tissue contained substantially lower densities of labeled EF1 at early times, compared with other organs. This finding is; consistent with the expected hydrophilicity of EF1, compared with EF5.

TABLE 2

Distribution of [$^{18}$F]EF-1 in murine tissues.

| Tissue | 5 minutes | 5 minutes | 90 minutes | 90 minutes |
|---|---|---|---|---|
| Blood | 0.041 | 0.038 | 0.005 | 0.007 |
| Brain | 0.004 | 0.004 | 0.003 | 0.005 |
| Muscle | 0.038 | 0.031 | 0.005 | 0.009 |
| Liver | 0.064 | 0.050 | 0.016 | 0.020 |
| Spleen | 0.034 | 0.035 | 0.005 | 0.007 |
| Kidney | 0.072 | 0.044 | 0.011 | 0.015 |
| Tibia | 0.045 | 0.042 | 0.079 | 0.064 |
| Cecum | 0.022 | 0.023 | 0.021 | 0.045 |
| Stomach | 0.013 | 0.013 | 0.007 | 0.009 |
| Intestine | 0.037 | 0.039 | 0.014 | 0.012 |
| Esophagus | | | 0.012 | |
| Urine | 0.045 | | 0.595 | 0.786 |
| Tail | 0.100 | 0.041 | 0.071 | 0.051 |
| Lung | 0.052 | 0.046 | 0.007 | 0.005 |
| Heart | 0.041 | 0.052 | 0.006 | 0.009 |

EXAMPLE 15

General Synthetic Method for Certain Compounds of the Invention

Brominated precursors to EF3 and EF5 wherein one of the terminal fluorines was substituted by bromine have now been made. Nucleophilic exchange reactions were attempted using the conditions described in Example 10, but problems arose because of the unusual chemical properties of multiply halogenated alkyl chains. The problems were diametrically opposed for the two precursors. For the EF3 precursor, named EF2Br (sidechain ending in —CH$_2$CF$_2$Br), rapid bromine elimination occurred because of the ease with which hydrogen can be co-eliminated from the adjacent carbon. For the EF5 precursor, named EF4Br (sidechain ending in CF$_2$CF$_2$Br) the bromine-carbon bond is highly stabilized and exchange conditions must be sufficiently harsh that the core 2-nitroimidazole structure is destroyed. The invention employs new chemical methods because previous work done to produce molecules suitable for PET imaging have not novel involved structures of the kind claimed. Essentially, the degree of halogen saturation on the terminal carbon has been modified to allow fluorine for bromine substitution while minimizing bromine elimination and/or molecular destruction under conditions suitable for such substitution (hot DMSO with fluoride carrier).

What is claimed is:

1. A Method for detecting tissue hypoxia in a mammal comprising: administering to mammal a compound having the formula:

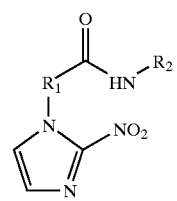

wherein R$_1$ is CH$_2$ and R$_2$ is an alkyl group having the formula CH$_2$CH$_2$X, wherein X is halogen or hydrogen, Y is CHF$_2$ or CH$_2$F, wherein at least 1 carbon atom of said alkyl group is bound with at least one $^{18}$F; and imaging the portion of the mammal containing the tissue.

2. The method of claim 1 wherein the detection technique is PET.

3. The method of claim 1 wherein $R_2$ is $CH_2CH_2CH_2{}^{18}F$ and the detection technique is PET.

4. The method of claim 1 wherein the halogen is fluorine.

5. The method of claim 1 wherein $R_2$ is $CH_2CF_2CH_2{}^{18}F$.

6. The method of claim 1 wherein $R_2$ is $CH_2CF_2CH^{18}F_2$.

7. The method of claim 1 wherein $R_2$ is $CH_2CHFCH_2{}^{18}F$.

8. The method of claim 1 wherein $R_2$ is $CH_2CHFCH^{18}F_2$.

9. The method of claim 1 wherein $R_2$ is $CH_2CH_2CH^{18}F_2$.

* * * * *

UNITED STATES PATENT AND TRADEMARK OFFICE
CERTIFICATE OF CORRECTION

PATENT NO. : 6,855,828 B1
DATED : February 15, 2005
INVENTOR(S) : Cameron J. Koch et al.

It is certified that error appears in the above-identified patent and that said Letters Patent is hereby corrected as shown below:

Title page,
Item [56], References Cited, OTHER PUBLICATIONS,
"Beaman et al." reference, please delete "dderivatives" and insert -- derivatives -- therefor.
"Knauf et al." reference, please delete "asociated" and insert -- associated -- therefor.
"Koch, C.J. et al." reference, please delete "Nonprotien" and insert -- Nonprotein -- therefor.
"Cobb, L.M. et al." reference, please delete "19982," and insert -- 1992, -- therefor.
"Siim, B.G., et al." reference, please delete "trasplanted" and insert -- transplanted -- therefor.

Column 2,
Line 61, please delete "minidazole" and insert -- misonidazole -- therefor.

Column 3,
Line 13, please delete "MR)" and insert -- MRI) -- therefor.

Column 9,
Line 53, please delete "starring" and insert -- starting -- therefor.
Line 54, please delete "staring" and insert -- starting -- therefor.

Column 10,
Line 19, please delete "OFF" and insert -- $^{18}$F -- therefor.

Column 11,
Line 10, please delete "diners" and insert -- dimers -- therefor.

Column 14,
Line 5, please delete "J=41 Hz," and insert -- J=4 Hz, -- therefor.

Column 15,
Line 36, please delete "dimethyliraidazolinone." and insert -- dimethylimidazolinone. -- therefor.
Line 45, please delete "reaction using enriched" insert -- reaction using $^{18}$O- enriched -- therefor.

Column 16,
Line 11, please delete "solution At" and insert -- solution. At -- therefor.

UNITED STATES PATENT AND TRADEMARK OFFICE
CERTIFICATE OF CORRECTION

PATENT NO. : 6,855,828 B1
DATED : February 15, 2005
INVENTOR(S) : Cameron J. Koch et al.

It is certified that error appears in the above-identified patent and that said Letters Patent is hereby corrected as shown below:

<u>Column 17,</u>
Line 24, please delete "was" and insert -- were -- therefor.
Line 26, please delete "weighted" and insert -- weighed -- therefor.

<u>Column 18,</u>
Line 40, please delete "have not novel involved" and insert -- have no novel involved -- therefor.
Line 60, please delete "wherein $R_1$ is $CH_2$" and insert -- wherein $R_1$ is $CH_2$- -- therefor.
Line 61, please delete "$CH_2CH_2X$," and insert -- $CH_2CX_2Y$, -- therefor.

Signed and Sealed this

Twenty-seventh Day of September, 2005

JON W. DUDAS
*Director of the United States Patent and Trademark Office*